US00PP12640P2

(12) United States Plant Patent
Carruth

(10) Patent No.: US PP12,640 P2
(45) Date of Patent: May 21, 2002

(54) HYBRID TEA ROSE PLANT NAMED 'WEKBIPUPOIS'

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/640,096

(22) Filed: Aug. 15, 2000

(51) Int. Cl.[7] ..... A01H 5/00
(52) U.S. Cl. ..... Plt./140
(58) Field of Search ..... Plt./130, 140, 139

*Primary Examiner*—Howard J. Locker
(74) *Attorney, Agent, or Firm*—Christie, Parker & Hale, LLP

(57) ABSTRACT

A new variety of Hybrid Tea rose suitable for garden decoration, having flowers of deep purple red coloration.

1 Drawing Sheet

BACKGROUND OF THE INVENTION

This invention relates to a new and distinct variety of Hybrid Tea Rose. The varietal denomination of the new variety is 'WEKbipupois'. It has as its seed parent the variety known as 'STEbigpu' (U.S. Plant Pat. No. 6,262) and as its pollen parent the variety known as 'AROpoiz' (U.S. Plant Pat. No. 6,812).

SUMMARY OF THE INVENTION

Among the features which distinguish the new variety from other presently available and commercial rose cultivars known to the inventor are the following combination of characteristics: its deep red purple flower coloration essentially as described and illustrated herein, its strong fragrance, its dark blushed peduncles and its stipules edged with numerous stipitate glands. The plant has an upright and somewhat spreading plant growth habit, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'WEKbipupois' may be asexually propagated by cuttings, budding or grafting.

COMPARISON WITH PARENTS

The new rose may be distinguished from its seed parent, 'STEbigpu', by the following combination of characteristics: whereas 'WEKbipupois' bears medium sized flowers with about 29 to 34 petals, 'STEbigpu' bears significantly larger flowers with higher petalage. The seed parent bears flowers with deep purple tones, whereas the new seedling bears flowers with significantly more red tones.

The new variety may be distinguished from its pollen parent, 'AROpoiz', by the following combination of characteristics: whereas 'WEKbipupois' bears medium sized flowers of red purple coloration, 'AROpoiz' bears significantly larger flowers of lavender coloration.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of August. Phenotypic expression may vary with environmental, cultural and climatic conditions, as well as differences in conditions of light and soil.

FLOWER

The new variety usually bears its flowers singly, sometimes in clusters of two or more per stem. Flowers may be borne in irregular somewhat rounded clusters on strong medium to long stems (about 45 to about 60 cms.). Outdoors, the plant blooms abundantly and nearly continuously during the growing season. The flowers have a strong citrus-like to spicy fragrance.

BUD

The peduncle is about 3.5 to about 5.0 cms. in length. It is moderately smooth, with some stipitate glands and fine hairs. Peduncle color is between 146B and 144A, often moderately suffused with between 184A and 183C.

Before the calyx breaks, the bud is about 1.6 to about 1.8 cms. in diameter at the widest point, about 2.5 to about 2.7 cms. in length, and pointed to ovoid in shape. The surface of the bud bears many stipitate glands and some fine hairs, usually with slender entire foliaceous parts extending beyond the tip of the bus about ¼ or more of its length. Bud color is between 146B and 144A.

The inner surface of the sepals is covered with fine wooly tomentum; sepal margins are lined with many stipitate glands and hairs.

As the petals open (after the calyx breaks), the bud is about 1.8 to about 2.1 cms. in diameter at the widest point, about 2.6 to about 2.9 cms. in length, and moderately pointed to urn-shaped in form. The color of the under and upper surfaces of the newly opened petals is between 59A and 53A. At the point where the petal attaches, there is a moderately small zone of between 2C and 4C.

BLOOM

When fully open, the bloom ranges from about 9 to about 10 cms. in diameter. Petalage is double with about 29 to 34 petals and about 2 to 7 petaloids arranged irregularly. When partially open, the bloom form is somewhat cupped to high centered, and the petals are moderately spiraled to cupped with petal edges somewhat reflexed outward. When fully open, the bloom form is more cupped to full, and the petals are more loosely cupped to somewhat undulated with petal edges moderately reflexed outward.

PETALS

The substance of the petals is moderately heavy and of medium thickness, with upper surfaces slightly satiny to velvety and under surfaces somewhat shiny to satiny. The outer petals are moderately broad and nearly round in shape with somewhat rounded apices. The inner petals are more broadly obovate in shape with somewhat rounded apices.

NEWLY OPENED FLOWER

The under and upper surface of the outer, intermediate and inner petals is between 53A and 60A. At the point where the petal attaches, there is a small zone of between 4C and 8C.

The general tonality of the newly opened flower is between 53A and 60A.

THREE DAY OLD FLOWER

The under and upper surface of the outermost petals is between 60A and 61A. The under and upper surface of the inner petals is between 59C and 61B. At the point where the petal attaches, there is a small zone of near 11D.

The general tonality of the three day old flower is between 59C and 61B with slightly darker tones on the outermost petals.

On the spent bloom, the petals usually drop off cleanly.

In August in Upland, Calif., blooms on the bush growing outdoors generally last about four to five days. Cut roses from plants grown outdoors and kept at normal indoor living temperatures generally last about four to five or more days.

MALE REPRODUCTIVE ORGANS

Stamens are average in number (average about 90) and are arranged regularly about the pistils; a few are mixed with petaloids. The filaments are of irregular length and very thin caliper, most with anthers. Filaments are near 155B in color. The anthers open approximately at the same time. Anther color is near 16A when immature and near 165C at maturity. Pollen is moderate to abundant and near 11C in color.

FEMALE REPRODUCTIVE ORGANS

Pistils vary in number (average about 75). The styles are moderately short to uneven in length and somewhat tightly bunched. Stigma color is near 8C. Style color is of similar coloration, often lightly suffused with near 45D. Ovaries are usually all enclosed in the calyx.

Hips are of moderately short to average length, somewhat flat to globular in form, and near 26B in color when ripe. The hip surface is very smooth with very thick fleshy walls. There are approximately 7 to 16 medium to large seeds per hip.

FOLIAGE

The compound leaves are usually comprised of three to five leaflets and are borne abundantly. The five-leaflet leaves at about 6 to about 10 cms. in length and about 5.5 to about 8 cms. in width at the widest point and matte in finish. The terminal leaflets are about 3.5 to about 5 cms. in length and about 2.4 to about 3.1 cms. in width at the widest point, oval in shape with moderately acute apices and somewhat round to acute bases. Their margins are usually simply serrate.

The upper surface of the mature leaf is between 147A and 139A. The under surface of the mature leaf is between 147C and 195A. The upper surface of the young leaf is between 146A and 146C, usually moderately suffused with between 183A and 183C. The under surface of the young leaf is of similar colorations but more heavily suffused with the darker pigment.

The rachis is of average to light caliper. The upper side is shallowly grooved with some hairs and few stipitate glands. The under side of the rachis is very smooth with few hairs and very few stipitate glands.

The stipules are about 1.1 to about 1.5 cms. in length and of medium width with straight points that usually turn out at an angle of less than 45 degrees. The stipules are often edged with numerous stipitate glands.

The plant displays an average degree of resistance to powdery mildew and rust as compared to other commercial varieties grown under comparable conditions in Upland, Calif.

GROWTH

The plant has an upright somewhat spreading medium height to tall growth habit (about 125 to about 150 cms. in height and about 90 to about 120 cms. spread at the widest point), with moderately full branching.

The color of the major stems is near 148A. They bear few large prickles that are about 0.3 to about 0.7 cms. in length. The large prickles are almost straight, hooked slightly downward with a moderately narrow oval base; prickle color is near 166C. The major stem bears very few small prickles of similar shape and coloration.

The color of the branches is between 146B and 148A. They bear several large prickles, which are of similar size and shape to the large prickles on the major stems; prickle color is between 164A and 165C. The branches bear few small prickles of similar shape and coloration.

The color of the new shoots is between 144A and 146C often suffused with between 183B and 183D. They bear several large prickles, which are of similar size and shape to the large prickles on the major stems; prickle color is near 160A often suffused with near 183D. The shoots bear few small prickles of similar shape and coloration.

I claim:

1. A new and distinct Hybrid Tea rose plant of the variety substantially as described and illustrated herein.

* * * * *

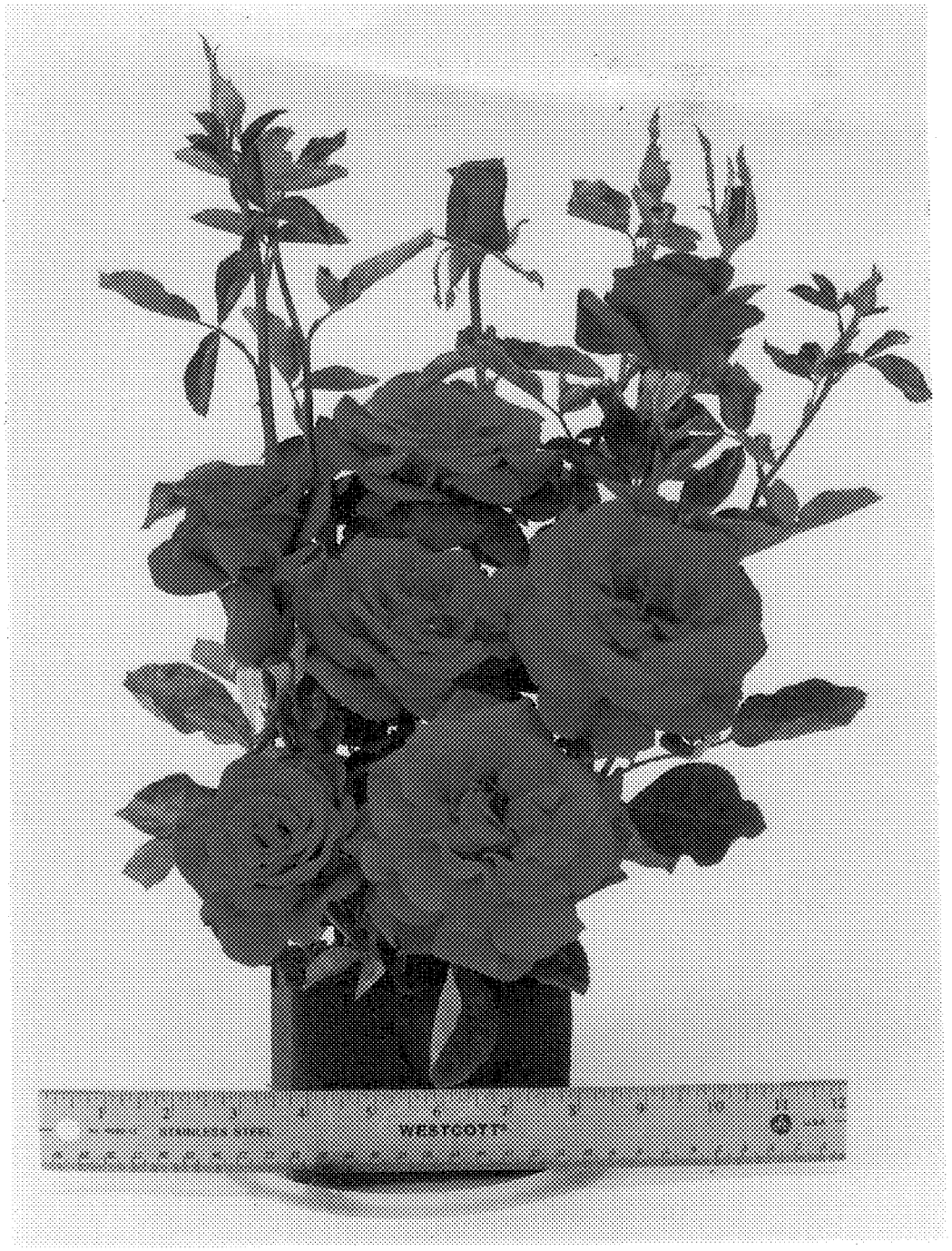
WESTCOTT